United States Patent
Amick et al.

(10) Patent No.: US 6,437,020 B1
(45) Date of Patent: Aug. 20, 2002

(54) POLYMER STABILIZATION

(76) Inventors: David Richard Amick, 186 Pine Valley Rd., Doylestown, PA (US) 18901; Jerome Michael Harris, 1101 Townshipline Rd., Penllyn, PA (US) 19422; John Robert Mattox, 637 Cedar La., Perkasie, PA (US) 18944

( * ) Notice: Subject to any disclaimer, the term of this patent is extended or adjusted under 35 U.S.C. 154(b) by 17 days.

(21) Appl. No.: 09/734,138

(22) Filed: Dec. 11, 2000

Related U.S. Application Data

(60) Provisional application No. 60/172,947, filed on Dec. 21, 1999.

(51) Int. Cl.$^7$ .............................. C08K 5/45; C08K 5/34; C08K 5/17; C08K 5/33
(52) U.S. Cl. ........................... 523/122; 524/84; 524/99; 524/236
(58) Field of Search ............................ 523/122; 524/84, 524/99, 236

(56) References Cited

U.S. PATENT DOCUMENTS

| | | |
|---|---|---|
| 3,926,909 A | 12/1975 | Wei |
| 4,079,028 A | 3/1978 | Emmons et al. |
| 4,426,485 A | 1/1984 | Hoy |
| 4,499,233 A | 2/1985 | Tetenbaum et al. |
| 4,876,174 A * | 10/1989 | Ishikawa et al. ............ 430/380 |
| 4,920,137 A | 4/1990 | Segall et al. |
| 4,929,660 A | 5/1990 | Chen |
| 5,352,712 A | 10/1994 | Shustack |
| 5,444,078 A | 8/1995 | Yu et al. |
| 5,599,827 A | 2/1997 | Gironda |
| 5,703,105 A * | 12/1997 | Redlich et al. ............. 514/372 |

OTHER PUBLICATIONS

Encyclopedia of Polymer Science and Engineering, vol. 6, John Wiley and Sons, New York, pp. 252–253 (1986).

* cited by examiner

*Primary Examiner*—Kriellion A. Sanders
(74) *Attorney, Agent, or Firm*—S. Matthew Cairns

(57) ABSTRACT

Disclosed are stable polyurethane thickener compositions and methods for stabilizing such compositions. Stabilized microbicide compositions and methods for stabilizing such microbicides are disclosed. Also disclosed are stable polyurethane thickener compositions containing microbicides.

12 Claims, No Drawings

POLYMER STABILIZATION

CROSS REFERENCE TO RELATED PATENT APPLICATIONS

This is a non-provisional application of prior pending U.S. provisional application serial No. 60/172,947 filed Dec. 21, 1999.

BACKGROUND OF THE INVENTION

This invention relates generally to the stabilization of certain polymers. In particular, this invention relates to the stabilization of certain water-based urethane polymers.

Latticies and other aqueous systems can require thickening, that is their viscosity must be increased, for certain processing conditions and certain end uses. Such thickeners often impart or improve other properties as well. For example, thickeners are used in latex paints not only for viscosity improvement and control, but also for protective colloidal action and for improvement of pigment suspension, leveling and flow. In addition, the thickeners often emulsify, disperse and stabilize latex ingredients and are themselves film formers. Such thickening additives can also improve the sticking of binding properties of the composition.

Typically, thickening agents are commercially available as either "solvent grade" or "water grade." Solvent grade thickeners refer to those thickeners dissolved or dispersed in a mixture of water and organic solvent. Water grade thickeners refer to those thickeners that are dissolved or dispersed in water.

One well-known class of such thickening agents are the low molecular weight polyurethanes. Such polyurethane thickeners are typically nonionic. For example, U.S. Pat. No. 4,079,028 (Emmons) discloses non-ionic polyurethanes having at least three low molecular weight hydrophobic groups at least two of which are terminal (external) hydrophobic groups.

Many commercially available thickeners, such as polyurethane thickeners, contain ethylene oxide chains. Under certain processing conditions, these commercial thickeners, both solvent and water grades, suffer from degradation of the ethylene oxide chain. Once such degradation occurs, the thickener loses some or all of its viscosity improving ability. Certain stabilizers, such as butyrated hydroxytoluene ("BHT") have been added to stabilize solvent grade thickeners. For example, the *Encyclopedia of Polymer Science and Engineering,* vol. 6, John Wiley & Sons, New York, page 252 (1986), discloses that poly(ethylene oxide) compounds can be stabilized against degradation through the use of 0.01 to 0.5 percent by weight phenothiazine, BHT, or butyrated hydroxyanisole ("BHA"). Such stabilizers are not effective at stabilizing water grade polyurethane thickeners.

Commercially available thickeners, particularly water grade thickeners, also suffer from microbial attack. Microbicides have been used to preserve water grade thickeners against microbial attack. One class of microbicides that is particularly suited to the stabilization of thickeners is 3-isothiazolones, and in particular a 3:1 mixture of 5-chloro-2-methyl-3-isothiazolone and 2-methyl-3-isothiazolone.

While 3-isothiazolones are very effective microbicides, they suffer from being unstable under certain conditions, particularly in the presence of nucleophiles. Without the presence of a stabilizer, many 3-isothiazolones chemically degrade and lose microbicidal efficacy. For example, U.S. Pat. No. 5,599,827 (Gironda) discloses the stabilization of 5-chloro-2-methyl-3-isothiazolone and/or 2-methyl-3-isothiazolone by forming a microemulsion with organic solvents having less than 6 percent by weight solubility in water and anionic surfactants. However, such stabilized isothiazolones are costly to use and introduce other components, such as different or unwanted surfactants, into the polyurethane thickener composition.

U.S. Pat. No. 4,920,137 (Segall) discloses various substituted phenyl compounds as stabilizers for 3-isothiazolones. However, such stabilizers are not very effective in stabilizing 3-isothiazones in aqueous compositions. Also, undesired precipitate may occur in aqueous 3-isothiazolone compositions stabilized with these substituted phenyl compounds.

Thus, there is a continuing need to stabilize water grade polyurethane thickeners, to stabilize 3-isothiazolone compounds, and particularly to stabilize both polyurethane thickeners and 3-isothiazolone compounds in combination.

SUMMARY OF THE INVENTION

The inventors have surprisingly found that diethyl hydroxyl amine and 4-hydroxy-2,2-6,6-tetramethylpiperidinoxyl reduces the degradation of water grade polyurethane thickeners. It has been further surprisingly found that diethyl hydroxyl amine and 4-hydroxy-2,2-6,6-tetramethylpiperidinoxyl stabilize the 3-isothiazolone microbicides used in such water grade polyurethane thickeners.

In one aspect, the present invention provides a composition including one or more water grade polyurethane thickeners, water, a stabilizer including diethyl hydroxyl amine or 4-hydroxy-2,2-6,6-tetramethylpiperidinoxyl, and optionally one or more 3-isothiazolone microbicides, wherein the composition is substantially free of organic solvent.

In a second aspect, the present invention provides a method for stabilizing thickening agent compositions including one or more polyurethane thickening agents including the step of contacting the composition with a stabilizer including diethyl hydroxyl amine or 4-hydroxy-2,2-6,6-tetramethylpiperidinoxyl, wherein the composition optionally includes one ore more 3-isothiazolone microbicides and wherein the composition is substantially free of organic solvent.

In a third aspect, the present invention provides a latex composition including the stabilized polyurethane thickener composition described above.

In a fourth aspect, the present invention provides a stable microbicide composition including one or more 3-isothiazolone compounds and a stabilizer including diethyl hydroxyl amine or 4-hydroxy-2,2-6,6-tetramethylpiperidinoxyl.

In a fifth aspect, the present invention provides a method for stabilizing a microbicide including the step of contacting one or more 3-isothiazolone compounds with a stabilizer including diethyl hydroxyl amine or 4-hydroxy-2,2-6,6-tetramethylpiperidinoxyl.

DETAILED DESCRIPTION OF THE INVENTION

As used throughout this specification, the following abbreviations shall have the following meanings, unless the context clearly indicates otherwise: g=gram; °C.=degrees Centigrade; mL=milliliter; wt %=weight percent; ppm=parts per million; and DI=deionized.

The terms "thickener" and "thickening agent" are used interchangeably throughout this specification. As used herein, the term "polymer" refers to the water grade polyurethanes of the present invention. The term "microbicide" refers to a compound capable of inhibiting the growth of or controlling the growth of microorganisms at a locus. The term "microorganism" includes, but is not limited to, bacteria, fungi and algae. "Preservative" and "microbicide" are used interchangeably throughout this specification.

As used throughout this specification, the term "hydrophobe" includes not only the hydrocarbon residues of hydroxyl, amino or isocyanate reactants, but also the combination of such residues with the next adjacent urethane and other groups remaining in the structure after reaction. The term "hydrophobe" refers to all those portions or segments of the polymeric reaction products which contribute to water insolubility. All portions or segments other than the residues of the polyether polyol reactants therefore are hydrophobic.

All amounts are percent by weight and all ratios are by weight, unless otherwise noted. All numerical ranges are inclusive.

The stable water grade thickener compositions of the present invention include one or more polyurethane thickeners, water and a stabilizer including diethyl hydroxyl amine or 4-hydroxy-2,2-6,6-tetramethylpiperidinoxyl, wherein the composition is substantially free of organic solvent. By "substantially free" of organic solvent is meant that the composition contains about 5 percent or less by weight organic solvent, based on the total weight of the composition. It is preferred that the water grade thickeners of the present invention are essentially free of organic solvent, that is, that the compositions contain about 2 percent or less by weight organic solvent, based on the total weight of the composition. It is further preferred that the water grade thickeners of the present invention are free of organic solvent.

Any polyurethane thickener that is water soluble or can be dispersed in water is suitable for use in the present invention. Suitable polyurethanes for use in the present invention include, but are not limited to those disclosed in U.S. Pat. Nos. 4,079,028; 5,023,309 (Kruse et al.); U.S. Pat. No. 4,499,233 (Tetenbaum et al.) and U.S. Pat. No. 4,426,485 (Hoy et al.), all of which are herein incorporated by reference.

Typically, polyurethane thickeners having more than 30 ethylene oxide ("EO") units and a hydrophobe containing a carbon chain having less than eight carbons are water soluble. Polyurethane thickeners having a hydrophobe containing eight carbons or greater must be "compatibilized" in order to be dissolved or dispersed in water. Such compatibilization is typically achieved through the use of a compatibilizer. A compatibilizer is any compound which prevents or reduces self-association of the polyurethane thickener when the thickener is combined with water. Such compatibilizers are known to those skilled in the art.

Suitable polyurethane thickeners for use in the present invention include, but are not limited to, nonionic polyurethanes having at least three low molecular weight hydrophobic groups at least two of which are terminal (external) hydrophobic groups. It will be appreciated by those skilled in the art that the polyurethanes of the present invention may contain one or more internal hydrophobic groups. Typically, the hydrophobic groups together contain a total of at least 20 carbon atoms and are linked through hydrophylic (water soluble) groups containing polyether segments of at least about 1500, preferably at least about 3000 molecular weight each so that the polyurethanes readily solubilize in water or can be dispersed in water, either with or without a compatibilizer. In general, the molecular weight of the polyurethanes is about 10,000 to about 200,000.

Particularly useful polyurethane thickeners are those disclosed in U.S. Pat. No. 4,079,028, herein incorporated by reference to the extent it teaches the preparation and use of such thickeners. Typically, the polyurethane polymers of the present invention are prepared in non-aqueous media and are the reaction products of at least reactants (a) and (c) of the following reactants: (a) at least one water soluble polyether polyol, (b) at least one water insoluble organic polyisocyanate, (c) at least one monofunctional hydrophobic organic compound selected from monofunctional active hydrogen compounds and organic monoisocyanates, and (d) at least one polyhydric alcohol or polyhydric alcohol ether. The products formed include the following:

1. Reacton products of a reactant (a) containing at least three hydroxyl groups, and the foregoing organic monoisocyanates;
2. Reaction products of reactant (a), reactant (b) containing two isocyanate groups, and the foregoing active hydrogen containing compounds, such as those wherein the ratio of equivalents of (a) to (b) is 0.5:1 to 1:1;
3. Reaction products of reactant (a), reactant (b) containing at least three isocyanate groups, and the active hydrogen containing compounds;
4. Reaction products of reactant (a), reactant (b) and the organic monoisocyanates; and
5. Reaction products of reactants (a), (b), (d) and the organic monoisocyanates.

By "monofunctional active hydrogen compound" is meant an organic compound having only one group which is reactive with isocyanate, such group therefore containing an active hydrogan atom, any other functional groups, if present, being substantially unreactive to isocyanate. Such compounds include monohydroxy compounds such as alcohols, alcohol ethers and monoamines, as well as polyfunctional compounds providing the compound is only monofunctional to isocyanates. For example, the primary amines, although difunctional in many reactions, are only monofunctional towards isocyanates, the hydrogen atom in the resulting urea group being relatively unreactive to isocyanate as compared with the hydrogen atom of the amino group or of unhindered alcohols.

Reactant (c) is a "capping" compound, meaning it reacts with ("caps") the terminal functional groups of the reaction product of reactants (a) and (b). The polyether polyol reactant (a) is an adduct of an alkylene oxide and a polyhydric alcohol or polyhydric alcohol ether, a hydroxyl-terminated prepolymer of such adduct and an organic polyisocyanate, or a mixture of such adducts with such prepolymers.

Reactant (d) may be employed to terminate isocyanate functionality or to link isocyanate-terminated reaction intermediates. Reactant (d) may be a polyhydric alcohol or polyhydric alcohol ether of the same type as used to form the adducts of reactant (a). The polyhydric alcohols or alcohol ethers may be aliphatic, cycloaliphatic or aromatic and may be used singly or in mixtures of either type or mixtures of the two types.

The organic polyisocyanates include simple di- and triisocyanates, isocyanate-terminated adducts of such polyhydric alcohols and organic di- or triisocyanates, as well as isocyanate-terminated prepolymers of polyalkylene ether glycols and organic di- or triisocyanates.

The hydrophobic groups of the polyurethanes occur in the residues of reactants (b) and (c) and may also occur in the residue of reactant (d) if present. The terminal (external) hydrophobes are the residues of the monofunctional active hydrogen compounds, organic monoisocyanates, or combinations of the residues of such compounds.

Typically, the water grade polymeric thickeners of the present invention are polyurethanes which may be classified as linear products (Group A), star-shaped products (Group B) or complex polymers (Group C).

Suitable linear products are those of the formula

A—$B_p$—$E_q$—(B—E)$_m$—$B_r$—$E_t$—A where each of p, q, r and t independently is zero or 1; at least one of q and r is 1; and t is zero when r is zero; provided that, when q is 1, then a) each of p, r and t is zero (as in formula I, below); or b) p is zero and each of r and t is 1 (as in formula II, below); or c) t is zero and each of r and p is 1 (as in formula III, below); and when q is zero, then r is 1 and each of p and t is zero (as in formula IV, below).

Polymers coming within the foregoing linear products formula include, but are not limited to:

I. A—E—(B—E)$_n$—A

II. A—E—(B—E)$_n$—B—E—A

III. A—B—E—(B—E)$_n$—B—A

IV. A—(B—E)n-B—A

The equivalent ratio of total active hydrogen to total isocyanate in the Group A compounds is about 1:1 to 2:1.

Suitable star-shaped products are those of the formula

[H—E—OCH$_2$]$_s$—L—[Q$_v$—(D$_u$—E—A)$_w$—R$_z$]$_m$ wherein L is X, Y or —O—; Q is —CH$_2$C≡; D is —CH$_2$O—; m is 2–4; s is zero to 2; m+s is the valence of L (2–4); w is 1–3, and each of u and z is independently zero or 1; and where X is a hydrocarbon radical containing at least 1 carbon atom, preferably 1–4 carbon atoms; and Y is a trivalent radical selected from OCONH(CH$_2$)$_6$N[CONH(CH$_2$)$_6$NHC(O)O]$_2$—; CH$_3$C[CH$_2$O—OCNHC$_7$H$_6$NHC)]$_3$—; and CH$_3$CH$_2$C[CH$_2$O—OCNHC$_7$H$_6$NHCO]$_3$—; provided that, a) when L is X, then u and w are each 1, v and z are each zero, m+s=4, and m is at least 2 (as in formula V below); b) when L is Y, then u, v and s are each zero, m is 3, w is 2–3, and z is zero or 1 (as in formula VI below); and c) when L is —O—, then v and u are each 1, w is 1–3, m is 2 and each of s and z is zero (as in formula VII below).

Polymers within the foregoing formula include, but are not limited to:

V. (H—E—OCH$_2$)$_s$—X—[CH$_2$O—E—A]$_m$

VI. Y[(E—A)$_w$R]$_3$

VII. O[CH$_2$C{CH$_2$O—E—A}$_3$]$_2$

In each of the polymers of Groups A and B: A and R are hydrophobic organic radicals containing at least one carbon atom; B is a divalent hydrophobic group of the structure

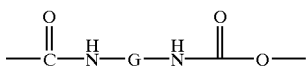

wherein G is the residue of an organic di- or triisocyanate, the residue having no remaining unreacted isocyanate groups; E is a divalent, hydrophillic, nonionic polyether group; and n is at least 1, such as about 1–20, preferably 1–10.

In structures V and VII, the equivalent ratio of total active hydrogen to total isocyanate is from about 1.2:1 to a stoichiometric excess of isocyanate; and in structure VI from about 1:1 to a stoichiometric excess of active hydrogen.

It will be apparent to the polymer chemist that values of n given in this specification are average rather than absolute values since in reaction products of the type of this invention, the reaction product will often be a mixture of several products having different values for n.

The star-shaped polymer configurations of formulas V-VII result from a polyhydric reactant such as trimethylolpropane or pentaerythritol (residue X in formula V) or a triisocyanate (residue Y in formula VI), or result from polyhydroxyether such as dipentaerythritol (Q and D of formula VII). L, Q and D form a central hydrophobic nucleus from which radiate hydrophilic polyether segments E, partially or fully capped (terminated) with hydrophobic groups A and R. The points or arms may have the same or different chain length and may contain hydrophobic segments alternating with hydrophilic portions. When s is greater than zero, partial capping results. In formulas V and VII, A is the residue of an organic monoisocyanate.

The complex polymer form of the polyurethanes of the present invention are complex mixtures of linear, branched and sub-branched products which form networks of hydrophobes and hydrophobic segments interspersed with hydrophilic segments. The products result from the multitude of different interactions which may take place between the polyfunctional reactants used to form them. The essential reactants are a polyfunctional compound containing at least three hydroxyl or isocyanate groups, a difunctional compound reactive with the polyfunctional compound, and a monofunctional reactant such as a monohydroxy or monoamino compound. The reactants may each be present singly or in mixtures of two or more. The difunctional compound is a diisocyanate (for reaction with the triol or higher polyol) or a diol (for reaction with the triisocyanate) and can also be present singly or in mixtures of two or more. The monohydroxy or monoamino compound, or mixture thereof, is added to the reaction mixture to cap isocyanate of the triisocyanate not reacted with the diol in order to prevent gelation. A monoisocyanate may be added to the reaction mixture if some of the polyol (diol, triol or higher polyol) remains unreacted or if it is desired to cap all hydroxyl groups.

It should be understood that in preparing the complex polymers of the present invention (Group C) as well as those of Groups A and B, capping of all hydroxyl is not required. Capping or hydrolyzing of all isocyanate, although not absolutely necessary, is preferred to avoid toxicity in the polymeric product. Generally, no more than about 25% of the hydroxyl should remain uncapped since the hydroxyl increases the water solubility and reduces thickening efficiency. Of course, if the product contains a relatively high proportion of hydrophobic residues a greater amount of uncapped hydroxyl can be tolerated.

In summary, the complex polymer products are polymeric compositions prepared by reacting: (a) a polyfunctional reactant selected from an organic polyol having at least three hydroxy groups, an organic polyisocyanate having at least three isocyanate groups, and mixtures thereof; (b) a difunctional reactant selected from an organic diol, an organic diisocyanate, and mixtures thereof, the diol being present in the reaction mixture when the polyisocyanate is present and the diisocyanate being present when the polyol is present; (c) a monofunctional hydroxyl or amino compound in an amount sufficient to cap any unreacted isocyanate remaining from the reaction of reactants a) and b) and to prevent gelation of the reaction mixture; and optionally d) a hydrophobic organic monoisocyanate to cap hydroxyl groups remaining from the reaction of reactants a) and b); wherein at least one of the polyol and diol contains at least one water soluble polyether segment of at least 1500 molecular weight, wherein the total carbon content of all hydrophobic groups is at least 20 and the average molecular weight of the polyurethane product is about 10,000–200,000.

As a general rule, the foregoing conditions are true for all of the polymers of Groups A, B and C. That is, the polymers will provide good thickening if the polyether segments have molecular weights of at least 1500 (preferably 3000 to 20,000), the polymers contain, on the average, at least three hydrophobic groups and at least two water soluble polyether segments linking the hydrophobes, the sum of the carbon atoms in the hydrophobic groups being at least 20, preferably at least 30, and the total molecular weight is about 10,000 to 200,000, preferably 12,000 to 150,000. The optimum polyether content will depend, of course, on the bulk and distribution of the hydrophobic groups in the polymer. Whereas a total polyether molecular weight of 4000 to 5000 may be suitable when the polymer contains small external and internal hydrophobes, the polyether content may have to be substantially increased when heavier and/or more extensively branched hydrophobic groups are to be built into the polymer, such as long chain fatty polyols or amines. About 200 carbon atoms in the hydrophobic portion is the practical upper limit although it will be understood that it is a relative matter since the proportion of polyether may be increased to offset increased hydrophobicity. However, as total molecular weight increases the viscosity increases and ease of handling decreases, and therefore the economic usefulness of the products is substantially diminished.

The stabilized polyurethane thickener compositions of the present invention are prepared by combining one or more polyurethane thickeners, water and a stabilizer including one or more of diethyl hydroxyl amine or 4-hydroxy-2,2-6,6-tetramethylpiperidinoxyl, wherein the compositions are substantially free of organic solvent. Typically, the stabilizer is added to the polyurethane thickener composition after the preparation of such thickener. However, other methods of combining the components of the compositions of the present invention are possible.

Any amount of stabilizer that stabilizes the polyurethane thickeners against degradation may be used in the compositions of the present invention. Typically, the amount of stabilizer compound is in the range of about 1 to about 5000 ppm, based on the total weight of the composition. Higher amounts of stabilizer compound may also be used advantageously, but at increased cost. It is preferred that the stabilizer compound is present in an amount in the range of about 10 to about 500 ppm, and more preferably about 50 to about 250 ppm.

It will be appreciated by those skilled in the art that the stabilizers of the present invention may be advantageously combined with other compounds that stabilize poly(ethylene oxide) compounds against degradation, such as phenothiazine, BHT and BHA. Such known stabilizers are typically used in an amount in the range of about 0.01 to 0.5 percent by weight.

One advantage of the stabilizers of the present invention is that they are effective in stabilizing polyurethane thickeners against degradation in very low amounts. In particular, the amount of the stabilizers of the present invention necessary to stabilize a polyurethane thickener is typically less than the amount of known stabilizer needed. A second advantage of the stabilizers of the present invention is that when such stabilizers are used in combination with known stabilizers, the amount of known stabilizer may be substantially reduced. A third advantage of the polyurethane thickener compositions of the present invention is that they are resistant to degradation at elevated temperatures, such as 50° C., and preferably 75° C., for an extended period of time. Such compositions of the present invention may be stable against degradation for up to 21 days, even at 75° C.

The water grade polyurethane thickener compositions of the present invention are substantially free of organic solvent, preferably essentially free of organic solvent, and more preferably free of organic solvent. It will be appreciated that small amounts of organic solvent, such as about 1 percent or less by weight based on the total weight of the composition, preferably about 0.5 percent or less, and more preferably about 0.25 percent or less, may be present in the compositions. Such small amounts of organic solvent may be present due to the presence of other additives in the composition.

The stabilizers of the present invention may also be used advantageously to stabilize solvent grade polyurethane thickeners. Such solvent grade thickeners typically contain one or more polyurethane thickening agents, water and organic solvent. Such organic solvents are typically present in an amount of about 10 percent by weight or greater, based on the total weight of the composition. Any water miscible organic solvent is suitable for use in solvent grade polyurethane thickeners. Suitable organic solvents include, but are not limited to, alkyl carbitols, glycols and the like. The amount of stabilizers useful in the solvent grade thickener compositions is the same amount useful in the water grade thickeners.

The water grade thickener compositions of the present invention may contain additional components, such as compatibilizers, preservatives and the like. It is preferred that the thickener compositions include one or more of compatibilizers and preservatives.

Particularly suitable preservatives for the water grade polyurethane thickeners of the present invention are the 3-isothiazolone microbicides. Suitable 3-isothiazolone microbicides include, but are not limited to: 5-chloro-2-methyl-3-isothiazolone, 2-methyl-3-isothiazolone, 2-n-octyl-2-isothiazolone, 4, 5-dichloro-2-n-octyl-3-isothiazolone, benzisothiazolone, 2-methyl-4, 5-trimethylene-3-isothiazolone, and mixtures thereof. One suitable mixture is 5-chloro-2-methyl-3-isothiazolone and 2-methyl-3-isothiazolone, and in particular a 3:1 ratio of 5-chloro-2-methyl-3-isothiazolone and 2-methyl-3-isothiazolone. Such 3-isothiazolones are generally commercially available, such as from the Rohm and Haas Company (Philadelphia, Pa.).

When used to preserve water grade polyurethane thickeners, it is preferred that the 3-isothiazolones are water-soluble, such as 5-chloro-2-methyl-3-isothiazolone and 2-methyl-3-isothiazolone, or if water-insoluble, such as 2-n-octyl-2-isothiazolone and 4,5-dichloro-2-n-octyl-3-isothiazolone, that they are formulated so as to be compatible with an aqueous system. Suitable formulations for the water-insoluble 3-isothiazolones are as emulsions or microemulsions, such as those disclosed in U.S. Pat. No. 5,444,078 (Yu et al.), herein incorporated by reference to the extent this patent teaches the preparation of such formulations.

Any amount of 3-isothiazolone microbicide that preserves the polyurethane thickener against microbial contamination is suitable for use in the present invention. Such 3-isothiazolones are typically used in an amount in the range of about 1 to 1500 ppm, preferably about 15 to about 500 ppm, and more preferably about 25 to about 125 ppm. The specific amount of 3-isothiazolone used will depend upon the particular 3-isothiazolone used as well as the other components in the composition, and such amount would be clear to one skilled in the art.

It will be appreciated by those skilled in the art that more than one preservative may be added to the compositions of the present invention. Thus, 3-isothiazolones may be effectively combined with another preservative. Both preservatives may be combined with the polyurethanes of the present invention.

The stabilized polyurethane thickener compositions of the present invention further including a preservative may be prepared by combining the polyurethane, water, stabilizer and preservative in any order. It is preferred that both the preservative and stabilizer be added to the polyurethane. The preservative may be added to the polyurethane prior to, simultaneously with, or after the addition of the stabilizer. In one embodiment, the stabilizer and preservative may be first combined together and then added to the polyurethane.

The polyurethane thickener compositions of the present invention are useful wherever a water based thickener is useful. In particular, the polyurethane compositions of the present invention are useful in emulsions, dispersions, and the like, and even more particularly in latex formulations, such as paint. For example, the polyurethane thickeners of the present invention may be added to polymer latex systems at any time during the preparation of such systems, including during or after polymerization or copolymerization and by single or multiple additions.

Typically, from about 0.1 to about 10 percent, and preferably 1 to 3 percent, by weight of the polymeric thickener on polymer latex solids is adequate to provide suitable levels of thickening and other properties.

However, the exact amount may be higher or lower depending on the particular system, other additives present and the like.

In another aspect, 3-isothiazolone microbicides may be effectively stabilized with one or more compounds including diethyl hydroxyl amine or 4-hydroxy-2,2-6,6-tetramethylpiperidinoxyl. Suitable 3-isothiazolone compounds are those described above.

Such stabilized 3-isothiazolone compositions typically include 0.5 to 35 percent by weight, based on the weight of the composition, of 3-isothiazolone; 0.01 to 20 percent by weight, based on the weight of the composition, of one or more compounds including diethyl hydroxyl amine or 4-hydroxy-2,2-6,6-tetramethylpiperidinoxyl; and solvent. It is preferred that the amount of 3-isothiazolone is in the range of 5 to 15 percent by weight, based on the weight of the composition. It is preferred that the amount of diethyl hydroxyl amine or 4-hydroxy-2,2-6,6-tetramethylpiperidinoxyl is in the range of 0.05 to 10 percent by weight, based on the weight of the composition, and more preferably 0.1 to 5 percent by weight.

Suitable solvents for the 3-isothiazolone compositions include one or more of, but are not limited to: water, alcohols, such as methanol, ethanol, propanol, and the like, esters, such as ethyl acetate, butyl acetate and the like, aromatic hydrocarbons, such as benzene, toluene, chlorobenzene, xylenes, and the like, carbonates, such as propylene carbonate, and glycols, such as ethylene glycol, diethylene glycol, polyethylene glycol, propylene glycol, dipropylene glycol, polypropylene glycol, and the like. It is preferred that the solvent is water or a mixture of water and glycol.

It will be appreciated by those skilled in the art that the stabilizers of the present invention may be advantageously combined with other known 3-isothiazolone stabilizers. Suitable known stabilizers for combination with the stabilizers of the present invention include, but are not limited to: iodic acid, periodic acid, iodate salts, such as sodium iodate, potassium iodate, lithium iodate and ammonium iodate, periodate salts, such as sodium periodate, potassium periodate, lithium periodate and ammonium periodate, and bromate salts, such as sodium bromate, potassium bromate, lithium bromate and ammonium bromate. It is preferred that the stabilizers of the present invention are combined with one or more other stabilizers, and more preferably combined with one or more of iodate salts, periodate salts and bromate salts.

Any amount of known 3-isothiazolone stabilizer may be combined with the stabilizers of the present invention. Typically, the ratio of 3-isothiazolone stabilizers of the present invention to known 3-isothiazolone stabilizers is in the range of 99:1 to 1:99, preferably 25:75 to 1:99, and more preferably 50:50 to 5:95.

The 3-isothiazolone compositions of the present invention may optionally contain one or more additives. Suitable additives include, but are not limited to: surfactants, thixotropic agents, anti-freeze agents, diluents, and the like. The amount of such optional additives depends upon the particular 3-isothiazolone composition and its intended use and is well known to those skilled in the art.

The stabilized 3-isothiazolone compositions of the present invention may be used to inhibit the growth of microorganisms by introducing a micrcobicidally effective amount of the compositions onto, into or at a locus subject to microbial attack. Suitable loci include, but are not limited to: cooling towers, air washers, boilers, mineral slurries, wastewater treatment, ornamental fountains, reverse osmosis filtration, ultrafiltration, ballast water, evaporative condensers, heat exchangers, pulp and paper processing fluids, plastics, emulsions and dispersions, paints, latexes, coatings, such as varnishes, construction products, such as mastics, caulks and sealants, adhesives, photographic chemicals, printing fluids, household products, cosmetics and toiletries, shampoos, soaps, detergents, industrial sanitizers, floor polishes, laundry rinse water, metalworking fluids, lubricants, hydraulic fluids, oil field fluids, fuel, drilling muds, leather products, textiles, wood, wood products, surfactant preservation, agricultural product preservation, diagnostic reagent preservation, pools and spas.

The stabilizers of the present invention are particularly useful in stabilizing one or more 3-isothiazolone compounds in a polyurethane thickener composition. Such polyurethane thickeners may be either water grade or solvent grade. It is preferred that the polyurethane thickener is a water grade thickener. An particular advantage of the stabilizers of the present invention is that they are very effective at stabilizing both polyurethane thickening agents and 3-isothiazolone preservatives in water grade polyurethane thickener compositions.

The following examples are presented to illustrate further various aspects of the present invention, but are not intended to limit the scope of the invention in any aspect.

EXAMPLE 1

To each of twelve (four sets of three) commercially available water grade Polyurethane Thickener A samples containing water, polyurethane and 25 ppm of a 3:1 mixture of 5-chloro-2-methyl-3-isothiazolone and 2-methyl-3-isothiazolone was added either diethyl hydroxyl amine ("DEHA") or 4-hydroxy-2, 2-6,6-tetramethylpiperidinoxyl ("TEMPOL") as stabilizer. Three samples of the commercially available Polyurethane Thickener A without the added stabilizers served as the controls. All the samples were stored at either 25° C. or in an oven at either 50° C. or 75° C. for 21 days. The samples were then removed from the oven and analyzed to determine any change in viscosity of the samples. The viscosity measurements were performed on a Brookfield viscometer at shear rates between 0.1 and 20 reciprocal seconds. The viscosity data are reported in the percentage of centapoise ("CPS") viscosity retained. The samples were also analyzed by reverse phase HPLC to determine the total amount of the 3-isothiazolones remaining. The results are reported in Tables 1 and 2.

TABLE 1

3-Isothiazolone Stability in Commercial Polyurethane Thickener A

| Temperature (° C.) | Control | DEHA (100 ppm) | DEHA (200 ppm) | TEMPOL (100 ppm) | TEMPOL (200 ppm) |
|---|---|---|---|---|---|
| 25 | 100 | 100 | 100 | 100 | 100 |
| 50 | 12 | 72 | 65 | 100 | 80 |
| 75 | 0 | 0 | 21 | 52 | 55 |

The above data clearly show that both DEHA and TEMPOL are effective stabilizers for 3-isothiazolones, particularly under the harsh storage conditions of 75° C.

TABLE 2

Stability of Polyurethane Thickener A in Percent CPS Viscosity Retained

| Temperature (° C.) | Control | DEHA (100 ppm) | DEHA (200 ppm) | TEMPOL (100 ppm) | TEMPOL (200 ppm) |
|---|---|---|---|---|---|
| 25 | 100 | 100 | 100 | 100 | 100 |
| 50 | 41 | 77 | 94 | 86 | 95 |
| 75 | 18 | 17 | 85 | 93 | 100 |

The above data clearly show that both DEHA and TEMPOL are effective at preventing the degradation of polyurethane thickeners, even under harsh storage conditions.

EXAMPLE 2

The procedure of Example 1 was repeated but replacing commercially available Polyurethane Thickener A with commercially available Polyurethane Thickener B. Polyurethane Thickener B had a lower average molecular weight than Polyurethane Thickener A and contained water, polyurethane and 25 ppm of a 3:1 mixture of 5-chloro-2-methyl-3-isothiazolone and 2-methyl-3-isothiazolone. The results are reported in Tables 3 and 4.

TABLE 3

3-Isothiazolone Stability in Commercial Polyurethane Thickener B

| Temperature (° C.) | Control | DEHA (100 ppm) | DEHA (200 ppm) | TEMPOL (100 ppm) | TEMPOL (200 ppm) |
|---|---|---|---|---|---|
| 25 | 100 | 100 | 100 | 100 | 100 |
| 50 | 9 | 35 | 35 | 34 | 26 |
| 75 | 0 | 2 | 29 | 0 | 20 |

The above data clearly show that both DEHA and TEMPOL are effective stabilizers for 3-isothiazolones as compared to the control sample.

TABLE 4

Stability of Polyurethane Thickner B in Percent CPS Viscosity Retained

| Temperature (° C.) | Control | DEHA (100 ppm) | DEHA (200 ppm) | TEMPOL (100 ppm) | TEMPOL (200 ppm) |
|---|---|---|---|---|---|
| 25 | 100 | 100 | 100 | 100 | 100 |
| 50 | 72 | 89 | 95 | 94 | 98 |
| 75 | 24 | 28 | 110 | 17 | 113 |

The above data clearly show that both DEHA and TEMPOL are effective at preventing the degradation of polyurethane thickeners, even under harsh storage conditions.

EXAMPLE 3

The procedure of Example 1 was repeated but replacing commercially available Polyurethane Thickener A with commercially available Polyurethane Thickener C. Polyurethane Thickener C had a higher average molecular weight than Polyurethane Thickener A and contained water, polyurethane and 25 ppm of a 3:1 mixture of 5-chloro-2-methyl-3-isothiazolone and 2-methyl-3-isothiazolone. The results are reported in Tables 5 and 6.

TABLE 5

3-Isothiazolone Stability in Commercial Polyurethane Thickner C

| Temperature (° C.) | Control | DEHA (100 ppm) | DEHA (200 ppm) | TEMPOL (100 ppm) | TEMPOL (200 ppm) |
|---|---|---|---|---|---|
| 25 | 100 | 100 | 100 | 100 | 100 |
| 50 | 16 | 29 | 32 | 57 | 66 |
| 75 | 0 | 22 | 30 | 45 | 74 |

The above data clearly show that both DEHA and TEMPOL are effective stabilizers for 3-isothiazolones as compared to the control sample.

TABLE 6

Stability of Polyurethane Thickner C in Percent CPS Viscosity Retained

| Temperature (° C.) | Control | DEHA (100 ppm) | DEHA (200 ppm) | TEMPOL (100 ppm) | TEMPOL (200 ppm) |
|---|---|---|---|---|---|
| 25 | 100 | 100 | 100 | 100 | 100 |
| 50 | 55 | 96 | 94 | 97 | 100 |
| 75 | 32 | 76 | 92 | 64 | 94 |

The above data clearly show that both DEHA and TEMPOL are effective at preventing the degradation of polyurethane thickeners, even at elevated storage temperatures.

EXAMPLE 4

Three samples of a 3:1 mixture of 5-chloro-2-methyl-3-isothiazolone and 2-methyl-3-isothiazolone were prepared as follows. Sample A (Control) contained 10% by weight of the 3-isothiazolone mixture and 90% by weight DI water. Sample B (Comparative) contained 10% by weight of the 3-isothiazolone mixture, 4% by weight potassium iodate stabilizer and 86% by weight DI water. Sample C (Invention) contained 10% by weight of the 3-isothiazolone mixture, 4% by weight potassium iodate stabilizer, 0.1% by weight 4-hydroxy-2,2-6,6-tetramethylpiperidinoxyl and the remainder as DI water. The samples were then stored in an oven at 40° C. and analyzed periodically by reverse phase HPLC to determine the amount of 5-chloro-2-methyl-3-isothiazolone remaining. The results are reported in Table 7.

TABLE 7

Percentage of 5-Chloro-2-methyl-3-isothiazolone Remaining

| Days of Storage | Sample A (Control) | Sample B (Comparative) | Sample C (Invention) |
|---|---|---|---|
| 7 | 85 | 100 | 101 |
| 28 | 66 | 97 | 99 |
| 42 | 56 | 94 | 99 |
| 77 | 14 | 83 | 98 |
| 105 | 23 | 76 | 94 |

The above data clearly indicate that 4-hydroxy-2,2-6,6-tetramethylpiperidinoxyl is an effective stabilizer for 3-isothiazolones.

EXAMPLE 5

Fifteen samples (D-R) containing DI water and a 3:1 mixture of 5-chloro-2-methyl-3-isothiazolone and 2-methyl-3-isothiazolone (the mixture referred to as "ITA") and one or more stabilizers. The compositions are shown in table 8. Sample D was the control, containing no stabilizers. Samples O to R were comparatives, each containing only a known 3-isothiazolone stabilizer. All samples were prepared in glass jars and stored in an oven at 55° C. The samples were periodically removed from the oven and analyzed by reverse phase HPLC to determine the percentage of 5-chloro-2-methyl-3-isothiazolone remaining. The results are reported in Table 9.

TABLE 8

3-Isothiazolone Compositions

| Sample | DI Water | ITA | TEMPOL | $KIO_3$ | $NaIO_3$ | $NaBrO_3$ | $NaClO_3$ |
|---|---|---|---|---|---|---|---|
| D* | 85.5 | 14.5 | 0 | 0 | 0 | 0 | 0 |
| E | 85.4 | 14.5 | 0.1 | 0 | 0 | 0 | 0 |
| F | 85.1 | 14.5 | 0.4 | 0 | 0 | 0 | 0 |
| G | 81.4 | 14.5 | 0.1 | 4.0 | 0 | 0 | 0 |
| H | 81.1 | 14.5 | 0.4 | 4.0 | 0 | 0 | 0 |
| I | 81.4 | 14.5 | 0.1 | 0 | 4.0 | 0 | 0 |
| J | 81.1 | 14.5 | 0.4 | 0 | 4.0 | 0 | 0 |
| K | 81.4 | 14.5 | 0.1 | 0 | 0 | 4.0 | 0 |
| L | 81.1 | 14.5 | 0.4 | 0 | 0 | 4.0 | 0 |
| M | 81.4 | 14.5 | 0.1 | 0 | 0 | 0 | 4.0 |
| N | 81.1 | 14.5 | 0.4 | 0 | 0 | 0 | 4.0 |
| O** | 81.5 | 14.5 | 0 | 4.0 | 0 | 0 | 0 |
| P** | 81.5 | 14.5 | 0 | 0 | 4.0 | 0 | 0 |
| Q** | 81.5 | 14.5 | 0 | 0 | 0 | 4.0 | 0 |
| R** | 81.5 | 14.5 | 0 | 0 | 0 | 0 | 4.0 |

*Control
**Comparative

TABLE 9

Percent of 5-Chloro-2-methyl-3-isothiazolone Remaining After Storage

| Sample | 8 Days | 15 Days | 53 Days | 60 Days | 73 Days |
|---|---|---|---|---|---|
| D* | 0 | —** | — | — | — |
| E | 0 | — | — | — | — |
| F | 0 | — | — | — | — |
| G | 97 | 86 | 0 | — | — |
| H | 102 | 103 | 96 | 1 | — |
| I | 100 | 92 | 0 | — | — |
| J | 103 | 101 | 98 | 91 | 89 |
| K | 99 | 93 | 1.4 | — | — |
| L | 101 | 97 | 0 | — | — |
| M | 46 | 0 | — | — | — |
| N | 103 | 100 | 0 | — | — |
| O*** | 98 | 85 | 0 | — | — |
| P*** | 98 | 83 | 0 | — | — |
| Q*** | 99 | 95 | 1 | — | — |
| R*** | 0 | — | — | — | — |

*Control
**Not analyzed
***Comparative

The above data clearly show that small amounts of 4-hydroxy-2,2-6,6-tetramethylpiperidinoxyl can be used to improve the effectiveness of known 3-isothiazolone stabilizers, such as sodium iodate.

What is claimed is:

1. A composition comprising one or more water grade polyurethane thickeners, water, a stabilizer comprising diethyl hydroxyl amine or 4-hydroxy-2,2-6,6-tetramethylpiperidinoxyl, and optionally one or more 3-isothiazolone microbicides, wherein the composition contains about 5 percent or less by weight organic solvent, based on the total weight of the composition.

2. The composition of claim 1 wherein the stabilizer is present in an amount of 1 to about 5000 ppm.

3. The composition of claim 2 wherein the stabilizer is present in an amount of 10 to about 500 ppm.

4. The composition of claim 1 wherein the 3-isothiazolone is a mixture of 5-chloro-2-methyl-3-isothiazolone and 2-methyl-3-isothiazolone.

5. A latex composition comprising the stabilized composition of claim 1.

6. A method for stabilizing thickening agent compositions comprising one or more polyurethane thickening agents comprising the step of contacting the composition with a stabilizer comprising diethyl hydroxyl amine or 4-hydroxy-2,2-6,6-tetramethylpiperidinoxyl, wherein the thickening agent optionally comprises one ore more 3-isothiazolone microbicides and wherein the composition contains about 5 percent or less by weight organic solvent, based on the total weight of the composition.

7. The method of claim 6 wherein the diethyl hydroxyl amine or 4-hydroxy-2,2-6,6-tetramethylpiperidinoxyl is present in an amount of 1 to about 5000 ppm.

8. The method of claim 6 wherein the 3-isothiazolone is a mixture of 5-chloro-2-methyl-3-isothiazolone and 2-methyl-3-isothiazolone.

9. A stable microbicide composition comprising one or more 3-isothiazolone compounds and a stabilizer comprising diethyl hydroxyl amine or 4-hydroxy-2,2-6,6-tetramethylpiperidinoxyl.

10. The microbicidal composition of claim 9 further comprising water.

11. The stable microbicide composition of claim 9 wherein the 3-isothiazolone compound is selected from the group consisting of 5-chloro-2-methyl-3-isothiazolone, 2-methyl-3-isothiazolone, 2-n-octyl-2-isothiazolone, 4,5-dichloro-2-n-octyl-3-isothiazolone, benzisothiazolone, 2-methyl-4,5-trimethylene-3-isothiazolone, and mixtures thereof.

12. A method for stabilizing a microbicide comprising the step of contacting one or more 3-isothiazolone compounds with a stabilizer comprising diethyl hydroxyl amine or 4-hydroxy-2,2-6,6-tetramethylpiperidinoxyl.

* * * * *